United States Patent

Huiku et al.

[11] Patent Number: 6,104,938
[45] Date of Patent: Aug. 15, 2000

[54] PROCEDURE, APPARATUS AND DETECTOR FOR THE DETERMINATION OF FRACTIONAL OXYGEN SATURATION

[75] Inventors: Matti Huiku; Kurt Weckström, both of Helsinki, Finland

[73] Assignee: Instrumentarium Oy, Helsinki, Finland

[21] Appl. No.: 09/011,625

[22] PCT Filed: Jun. 12, 1997

[86] PCT No.: PCT/FI97/00375

§ 371 Date: Feb. 12, 1998

§ 102(e) Date: Feb. 12, 1998

[87] PCT Pub. No.: WO97/47233

PCT Pub. Date: Dec. 18, 1997

[30] Foreign Application Priority Data

Jun. 12, 1996 [FI] Finland .................................. 962448

[51] Int. Cl.$^7$ ...................................................... A61B 5/00
[52] U.S. Cl. ........................................... 600/322; 600/328
[58] Field of Search .................................. 600/310, 320, 600/322, 323, 326, 328, 330

[56] References Cited

U.S. PATENT DOCUMENTS

| | | |
|---|---|---|
| Re. 35,122 | 12/1995 | Corenmann et al. . |
| 4,407,290 | 10/1983 | Wilber . |
| 4,621,643 | 11/1986 | New, Jr. et al. . |
| 4,653,498 | 3/1987 | New, Jr. et al. . |
| 4,700,708 | 10/1987 | New, Jr. et al. . |
| 4,714,341 | 12/1987 | Hamaguri et al. . |
| 4,770,179 | 9/1988 | New, Jr. et al. . |
| 4,819,752 | 4/1989 | Zelin . |
| 4,832,484 | 5/1989 | Aoyagi et al. . |
| 4,911,167 | 3/1990 | Corenman et al. . |
| 4,934,372 | 6/1990 | Corenman et al. . |
| 5,413,100 | 5/1995 | Barthelemy et al. . |
| 5,421,329 | 6/1995 | Casciani et al. . |
| 5,766,125 | 6/1998 | Aoyagi et al. . |

FOREIGN PATENT DOCUMENTS

| | | |
|---|---|---|
| 335357 | 10/1989 | European Pat. Off. . |
| 524083 | 1/1993 | European Pat. Off. . |
| 94/03102 | 2/1994 | WIPO . |

OTHER PUBLICATIONS

Arterial Oxygen Saturation by Non–Invasive Oximetry Technique: An Office Test for Determining Jeopardy of Status Asthmaticus, Leonard S. Girsh and Brian J. Girsh, Annuals of Allergy, vol. 42, Jan. 1979, pp. 14–16.

Primary Examiner—Eric F. Winakur
Attorney, Agent, or Firm—Andrus, Sceales, Starke & Sawall

[57] ABSTRACT

The invention relates to a procedure for determining the relative concentration or composition of different kinds of haemoglobin, such as oxyhaemoglobin, deoxyhaemoglobin and dyshaemoglobins, and/or dye components contained in blood in a non-invasive manner using the light absorption caused by different haemoglobin varieties and/or dye components, in which procedure light signals are transmitted at at least two predetermined wavelengths to a tissue comprised in the patient's blood circulation, the light signal transmitted through the target under measurement and/or reflected from it is received and the proportion of the intensity of the pulsating light signal received at each wavelength is determined in relation to the total intensity of the light transmitted through the tissue or reflected from the tissue. In the procedure, the effective extinction coefficients of blood haemoglobin derivatives and/or dye components in the tissue are determined for each light signal and/or light signal pair via a mathematical transformation from blood dye component extinction coefficients consistent with the Lambert-Beer theory and the proportion of specific blood haemoglobin derivatives and/or dye components in relation to the total amount of haemoglobin contained in the blood is determined by means of the intensity of the signals received in different wavelength ranges.

50 Claims, 7 Drawing Sheets

PROCEDURE, APPARATUS AND DETECTOR FOR THE DETERMINATION OF FRACTIONAL OXYGEN SATURATION

BACKGROUND OF THE INVENTION

The present invention relates to a procedure as defined and to a measuring apparatus for non-invasive determination of fractional oxygen saturation in blood. Moreover, the invention relates to a sensor, designed for use in conjunction with the measuring apparatus of the invention to collect measurement data about the patient.

Specifically, the present invention relates to the monitoring of the oxygenation level of the body in patient monitoring systems. Measuring the oxygen saturation of arterial blood in peripheral circulation is generally sufficient to determine the oxygenation situation and sufficiency of oxygen supply in the entire body. The oxygenation level of the human body can be estimated via oxygen saturation measurement of arterial blood either in a non-invasive manner using pulse oximeters or transcutaneous oximeters/blood gas analysers or in an invasive manner either by taking a sample of arterial blood and analysing in vitro blood gases (In Vitro Blood Gas/pH Analyzers) or performing an optic measurement on the blood sample using so-called CO-oximeters or haemoximeters (In Vitro Multiwavelength Oximeters).

Partial pressure measurements of gas in arterial blood samples and optic methods based on the absorption of light by blood samples are part of long-standing tradition, but clinical use of pulse oximeters only became common in late 1980's and the measuring principle itself is relatively new. There are numerous patents and patent applications relating to pulse oximeters. The most important of these as well as the most comprehensive general descriptions of prior art are found in patent specifications U.S. Pat. No. 4,653,498, U.S. Pat. No. 4,819,752, U.S. Pat. No. 4,407,290 and U.S. Pat. No. 4,832,484.

The prior-art technology described in the above-mentioned patent specifications, which is the basis of currently used equipment, is imperfect and inadequate for continuous and non-invasive monitoring of changes in the actual oxygenation level or degree of fractional oxygen saturation in a patient's blood. Although in vitro oximeters are in principle capable of measuring fractional oxygen saturation from a normal blood sample, the measurement is neither non-invasive nor continuous. On the other hand, pulse oximeters measure continuously and non-invasively, but they are not able to measure the actual degree of fractional oxygen saturation of blood and are therefore inadequate for situations where only a part of the total amount of haemoglobin in a patient is functional. Pulse oximeters measure fractional oxygen saturation assuming that the patient's blood composition is the same as that of a healthy, non-smoking person. A high dyshaemoglobin level, i.e. a high relative amount of haemoglobin not participating in oxygen transport, always involves a danger to the patient because current pulse oximeters produce an incorrect estimate of the oxygenation level of blood.

The cause of incorrect measurement lies in the measuring principle: Since pulse oximeters use only two different wavelengths of light for the estimation of oxygen saturation, only two different kinds of blood haemoglobin, viz. oxyhaemoglobin (HbO2) and deoxyhaemoglobin (Hb), can be accurately measured by this method. All other dyeing blood components (usually dyshaemoglobins or dyes used in clinical tests) have a disturbing effect on the measurement and can only be taken into account as average amounts. This type of average correction is generally made on the composition of healthy blood. However, the composition of normal blood may change in an unforeseen manner and without a readily identifiable cause. The blood composition of a patient with a critical illness may differ from the blood composition of a healthy person as a result of medication, the nature of the illness or a medical treatment or measurement. A new and significant treatment of this type is the so-called nitrogen oxide (NO) treatment, which may cause a considerable rise in the patient's methaemoglobin (MetHb) level. Another common case of incorrect measurement is carbon monoxide poisoning, which involves a high carboxyhaemoglobin (HbCO) level in the patient. Continuous non-invasive monitoring of the actual degree of oxygen saturation is particularly important during NO treatment because the dyshaemoglobin levels may rise relatively rapidly, which means that an analysis based on a blood sample is not sufficient. The measurement of fractional oxygen saturation is also of great importance in rescue operations and in follow-up monitoring after carboxyhaemoglobin poisoning.

It is obvious that accurate, continuous and non-invasive measurement of fractional oxygen saturation requires a sensor with several wavelengths used to produce an analysis of blood composition. In the following, prior art will be discussed by considering a technique that uses the principle of non-invasive measurement using an oximeter with several wavelengths.

A previously known oximeter based on non-invasive measurement uses eight different wavelengths to determine the average degree of oxygenation of the blood via a measurement on the ear (see Girsh et Girsh, Ann. Allergy, 42, pages 14–18, 1979). The measurement does not use the pulse oximeter principle, whereby the measurement is only applied to arterial blood by distinguishing from the light transmission a component pulsating in synchronism with the heartbeat and normalising this component against the total light transmission. Instead, average oxygen saturation is measured directly from the total light transmission at the wavelengths used. The total transmission depends on the oxygen saturation and composition of both arterial and venous blood, but also on the absorption and scattering caused by other tissues. Typically, blood accounts for only 1–2% of the amount of tissue, so the signal may be very ambiguous. Such a method has many drawbacks: First, the person's complexion, the structure of the tissue in itself and especially the scattering and absorption properties of the tissue as well as its other properties change and even dominate the total transmission. In fact, the method requires several wavelengths for the compensation of these properties, and it cannot produce reliable analyses of the composition of arterial blood. In addition, analysing the blood composition in terms of percentages is difficult because the relative amounts of arterial blood and venous blood and their different degrees of oxygen saturation affect the absorption. The amount of dyshaemoglobins is the same in both arteries and veins, but oxygen saturation varies with tissue metabolism and temperature or with the regulating mechanisms of the body.

In patents EP 335357 and U.S. Pat. No. 5,421,329 it is suggested that by adding a third wavelength to a conventional pulse oximeter with two wavelengths it is possible to improve the accuracy of functional saturation measurement with a pulse oximeter or to eliminate or reduce the artifacts caused e.g. by movement. In the former patent, the third wavelength is used to eliminate the irregular artifacts signal from on top of the pulsation caused by the heartbeat. The wavelength is not used for the determination or identification of the dyshaemoglobin level. In the latter patent, the third wavelength is used to adjust the measurement of a low degree of oxygen saturation, but it is not used in conjunction with the measurement of the normal saturation range or for the measurement of dyshaemoglobin levels or the degree of fractional oxygen saturation. The latter patent also relates to the reflection principle and especially to the measurement of oxygen saturation in a baby during childbirth. In this situation, a third wavelength is naturally needed to achieve a more reliable measurement. Similarly, patent application WO 94/03102 proposes the use of a third wavelength to eliminate artifacts caused by motion. Patent specification U.S. Pat. No. 4,714,341 (Minolta Camera) also uses a third wavelength for more accurate measurement of functional saturation. Like the others, this specification is not concerned with the measurement of fractional saturation or in general dyshaemoglobin levels.

Patent specification EP 0 524 083 also proposes the use of a third wavelength for simultaneous measurement of carboxyhaemoglobin level and oxygen saturation. In the measurement, three different laser diodes with wavelengths of 660 nm, 750 nm and 960 nm are used. These three wavelengths are used to measure the modulation ratios, and the concentrations of three unknown kinds of haemoglobin, HbO2, Hb and HbCO, are calculated by solving a linear system of equations. However, the procedure presented in patent specification EP 0 524 083 has two significant drawbacks. First, the procedure is not applicable for the measurement of MetHb; in other words, fractional saturation can only be determined for the three kinds of Hb mentioned above. Secondly, solving the aforesaid linear system of equations is not sufficient for the determination of the concentrations of the aforesaid three kinds of Hb, as will become evident later on from the description of a preferred embodiment of the calculating procedure of the present invention. The basic drawback is that the system of equations is not a linear one because the coefficients used in it are in themselves functions of the concentrations. For this reason, the use of this method is restricted to a very narrow range of oxygen saturation, and the procedure is not workable in the operating range generally required for pulse oximeters. In addition to the above drawbacks, the procedure involves the use of laser diodes and a fibre optic connection to the measurement point, which makes the measuring system rather too expensive for practical measurements and difficult for the user. Moreover, laser diodes have a narrow choice of wavelengths. Due to the use of fibre optics, the light is attenuated especially at the connection points and the signal-to-noise ratio is worse than in the conventional solution employing light-emitting diodes. The official regulations relating to coherent radiation and the danger caused by the radiation e.g. to the eye also constitute a limitation of the application of the procedure in practical situations.

Further, patent specification Aoyagi et al, EP 0 679 890 A1, representing prior art, presents an apparatus designed for the measurement of light absorbing blood components. According to the specification, the procedure and apparatus can be used to determine the degree of functional oxygen saturation of blood, the concentrations of different kinds of haemoglobin as well as other dye components of blood, such as bilirubin and in-vein dyes. The proposed procedure and apparatus are based on a rather unusual optical model of light transmission through tissue and formation of a pulsating signal. Since the procedure is obviously one of the prior-art solutions related to the present invention, it is necessary to point out the erroneous assumptions lying behind the procedure and apparatus. The drawbacks listed below serve as examples, and the drawbacks are not described in full extent. For a more detailed explanation of the drawbacks, reference is made to the thesis Reindert Graaff, "Tissue Optics Applied to Reflectance Pulse Oximetry", Groningen University, Feb. 12, 1993, which is an excellent description of tissue optics and its modern representation. To those familiar with pulse oximetry or non-invasive measurement of blood properties, the drawbacks listed below are self-evident and can be recognised via empirical measurements. Accordingly, patent application EP 0 679 890 is based on the following, erroneous propositions. First, diffusion approximation and its parametrised flux models (in the application referred to, the so-called Arthur Schuster theory) can be applied to describe the total transmission through tissue, but they cannot be used in conjunction with pulsating tissue components and the operation of pulse oximeters at short wavelengths (600–700 nm), nor can they generally be used at a low saturation or for highly absorptive blood dye components. Using the diffusion model (applies to situations where the scattering cross-section is considerably larger than the absorption cross-section) together with the Lambert-Beer pulse oximeter model (applies to situations where the absorption cross-section is considerably larger than the scattering cross-section) simultaneously generally does not lead to realistic results. Second, it is stated in the patent application that the scattering term is known and independent of the wavelength. In fact, the scattering term is one of the adjustable parameters in the model and is also dependent on the wavelength and the tissue type. The pulsating portion of the scattering is also dependent on the size, shape and number of blood cells, i.e. on the haematocrit. Third, the tissue term (in the patent application, the pulsating component that is not blood) plays no significant role in the signal formation at all and therefore it cannot be used in the way it appears in the formulas as a factor representing theoretical extinction coefficients of blood and empirically measured modulation ratios. Further, it is stated in the patent application that the tissue term is mostly water, which in fact does not absorb at all in relation to the dominating pulsating terms in the wavelength range used. In fact, the dominating pulsating tissue-type effect is produced by blood, whose absorption depends on all those things that patent application EP 0 679 890 presents as quantities to be measured, such as oxygen saturation, different haemoglobin varieties and their amounts and dyes; thus, there would be no linear correlation between different tissue terms that could be defined in advance—although the application asserts to the contrary—which means that the degree of non-linearity of the problem increases considerably. Fifth, the number of unknown quantities in the procedure and apparatus of the patent application in question clearly exceeds the number of equations available. Moreover, the patent application contains numerous other inaccuracies, so the application or the procedure and apparatus presented in it do not, at least in respect of their basic assumptions, meet the quality criteria that are expected to be observed in clinical patient monitoring measurements.

In the above, existing prior art has been dealt with from the point of view of systems using more than two different light sources each having a different spectral emission, yet so that the spectral emission in the same light source is always the same. Especially the use of more than two light sources is still associated with problems relating to maintaining the accuracy of the apparatus in use even in situations where the spectral emission of the light sources changes due to technical aspects of fabrication of the light source and maintaining accuracy requires a correction to compensate this change. A method for such correction or rather a cheap method for maintaining sensor accuracy is presented in U.S. Pat. No. 4,621,643 (December 1986), U.S. Pat. No. 4,700,708 (October 1987) and U.S. Pat. No. 4,770,179 (September 1988). All these patents propose solutions in which information about the wavelengths of the light sources is transmitted to the measuring apparatus by encoding the correction required by changes of wavelength into an impedance element or in practice into the resistance value of a resistor. From the resistance value or by some other similar coding method, the measuring apparatus receives information indicating the changes required in the calibration of the apparatus. This can be done with a single resistance value or other simple 'coding' when the unambiguity of the measurement signal is guaranteed via other techniques. In two-wavelength pulse oximeters, unambiguity is based on the apparatus forming substantially only one signal, i.e. a modulation ratio between the two wavelengths, a so-called R-value, which, via an unambiguous calibration curve, can be directly associated with the functional oxygen saturation or SpO2 value. No such unambiguous correlation exists when there are several light sources and more than two haemoglobin varieties or other blood dye components are to be measured. As a summary of prior art, it can be stated that so far there is no method or apparatus capable of reliable measurement of fractional oxygen saturation of arterial blood and quantitative determination of the dyshaemoglobin level.

SUMMARY OF THE INVENTION

The present invention proposes a different calibration method, which is unambiguous and is not—unlike prior-art technology—based on transmitting the emission properties of the light sources to a measuring apparatus but is instead based on light source-specific use of the absorption properties of each haemoglobin component or dye, i.e. the so-called extinction coefficients of blood. This allows e.g. situations where the wavelengths of the light sources or the light source type itself can be changed or the sensor can be aligned for different kinds of Hb or dye measurements while preserving the compatibility and accuracy of the sensor with all apparatus. Thus, in the framework of the present invention, the "wavelength" of the light source is understood in the first place as meaning the current number or other identification of the light source, which is associated with the haemoglobin components or dyes measured with the sensor in question. The new method is applicable both for sensors and apparatus with two light sources and for those with more than two light sources.

The object of the present invention is to eliminate the problems and inaccuracies described above. A specific object of the present invention is to produce an effective and accurate measuring procedure for the determination of the relative concentrations or compositions of haemoglobin derivatives or dye components contained in a patient's blood. A further object of the present invention is to produce a measuring apparatus and a sensor which can be utilised to effectively apply the calculation method of the present invention for determining the level of oxygen saturation in a patient's blood.

As for the features characteristic of the present invention, reference is made to the claims.

In the procedure of the invention for determining the relative concentration or composition of different kinds of haemoglobin contained in blood, such as oxyhaemoglobin, deoxyhaemoglobin and dyshaemoglobins, and/or dye components, such as various in-vein dyes or the like, in a non-invasive manner using the light absorption caused by different haemoglobin varieties and/or dye components, light signals are transmitted at at least two predetermined wavelengths to a tissue comprised in the patient's blood circulation, a light signal transmitted through the target under measurement and/or reflected from it is received and the proportion of the intensity of the pulsating light signal received at each wavelength is determined in relation to the total intensity of the light transmitted through the tissue or reflected from the tissue. The pulsation of the light signal is determined by the heartbeat frequency, which has a direct effect on the amount of blood flowing in the tissue and therefore also on the amount of haemoglobin derivatives and/or dye components.

According to the invention, the effective extinction coefficients of blood haemoglobin derivatives and/or dye components in the tissue are determined for each light signal and/or light signal pair via a mathematical transformation from the extinction coefficients of the blood dye components according to the Lambert-Beer theory and the proportion of specific blood haemoglobin derivatives and/or dye components in relation to the total amount of haemoglobin contained in the blood is determined by means of the intensity of the signals received at different wavelengths. Thus, the procedure of the invention is based on a so-called modulation signal for each wavelength and on a comparison of these signals between two different wavelengths. The result of the latter comparison is expressed in terms of a modulation ratio. This quantity describes the average blood dye difference between these two wavelengths. When this relative dye difference is measured using several wavelength pairs, the concentrations of different haemoglobin derivatives are obtained by solving a non-linear system of equations (1) formed from the wavelength pairs and extinction coefficients.

$$\begin{pmatrix} \%mod1 \\ \%mod2 \\ ... \\ \%mod3 \end{pmatrix}^* = C^*(T) \begin{pmatrix} \varepsilon_{11} & ... & \varepsilon_{1j} \\ \varepsilon_{21} & ... & \varepsilon_{2j} \\ & ... & \\ \varepsilon_{i1} & ... & \varepsilon_{ij} \end{pmatrix}_{ij} \cdot \begin{pmatrix} HbX_1 \\ HbX_2 \\ ... \\ HbX_j \end{pmatrix} \qquad (1)$$

where % mod i is the modulation percentage for light transmission as measured at wavelength i, i.e. the proportion of light transmission varying at heartbeat frequency as a percentage of the total light transmission;

C is a constant;

the ij-element of the T ($\epsilon$)-matrix is an empirical extinction coefficient of blood haemoglobin variety and/or dye component $HbX_j$, mathematically derived from the known extinction coefficient for wavelength i; and the unknown kinds of blood haemoglobin and/or dye components in percentages are placed in the vertical vector ($HbX_1, HbX_2, ..., HbX_j$). The non-linearity of the system of equations is due to divergences between theory, and practice. The actual extinction coefficients $\epsilon'$ are also dependent on the scattering of light caused by the tissue and on the combined effect of absorption and scattering. The corrections needed in the extinction coefficients are larger the larger is the proportion of the attenuation caused by absorption and scattering. In the Lambert-Beer theory, the scattering and the effect of the tissue are not taken into account.

The system of equations presented above can be solved in several advantageous ways according to the present invention. In an embodiment, the system of equations is solved for all blood dye components, the sum of whose proportions is 100%, and the number of independent light signals is selected so that it corresponds at least to the total number of haemoglobin derivatives and/or dye components set as unknowns. Moreover, it is to be noted that blood may also contain haemoglobin derivatives or dye components whose concentration and/or composition is known. In this case, the known concentrations must be taken into account when calculating the total number of all haemoglobin varieties and/or dye components.

In an embodiment of the present invention, the haemoglobin varieties set as unknowns are oxyhaemoglobin and deoxyhaemoglobin, and at least one dye component is a blood dyshaemoglobin variety, such as HbCO, MetHb or HbNO.

In an embodiment of the present invention, the non-linear system of equations is solved by using modulation ratios, wherein the transformation between the known extinction coefficients according to the Lambert-Beer theory and the effective extinction coefficient of the blood-containing tissue is a function transformation between the measured modulation ratio of two independent light signals and the modulation ratio formed from corresponding known extinction coefficients.

In an embodiment of the present invention, the non-linear system of equations is solved by dividing the non-linear system of equations into linear portions on the basis of blood composition and around a given composition and solving the linear system of equations thus obtained using experimentally determined extinction coefficients derived for the blood composition in question. The extinction coefficients are preferably determined in advance for different blood oxygenation levels. The non-linear system of equations thus reverts into a linear system of equations and it can be easily solved by known mathematical methods.

In a preferred embodiment, the non-linear system of equations is solved via an iterative process, part of which process consists in identifying the composition and/or existence of the dyshaemoglobin and/or dye that leads to the best iterative result. Iteration is a known mathematical method and is therefore not explained here in detail.

Further, in the determination of the concentrations of haemoglobin varieties and/or dye components, it is preferable to weight different modulation ratios on the basis of the patient's blood composition, in which case the non-linear system of equations (1) is solved iteratively by using weighted modulation ratios.

In a preferred embodiment of the present invention, a light signal is transmitted via the same or nearly the same optic route to the tissue using at least two predetermined wavelengths. As the light signal passes through the tissue at substantially the same point, errors due to divergences in the tissue are avoided.

The selection of wavelength ranges is explained below in greater detail by referring to FIG. 1, but in a preferred embodiment the wavelengths to be used are selected from four different wavelength ranges, of which at least one wavelength range is below 660 nm, preferably so that the wavelength ranges are: 620–650 nm, 655–665 nm, 680–750 nm and 790–1000 nm. The selection of wavelength ranges is further affected by the composition of human blood so that for a normal blood composition where the total amount of dyshaemoglobin is below a suitable level, e.g. below 3%, light signals produced at center wavelengths of 660 nm, 690 nm and 900 nm and/or modulation ratios formed from them are weighted in relation to the light signal in the wavelength range of 620–650 nm and its modulation ratios. For the measurement of a high methaemoglobin level, the wavelength range of 620–650 nm and its modulation ratios are used, which are weighted in substantially the same proportion as the other light signals used and their modulation ratios. In addition, for a normal composition of human blood, the measurement can be performed at four center wavelengths 900±10 nm, 690±5 nm, 658±5 nm and 632±5 or 900±10 nm, 690±5 nm, 658±5 nm and 645±5 nm.

In a preferred embodiment of the present invention, for each independent light signal an effective extinction coefficient is calculated in the light signal emission range concerned from wavelength correlations of known extinction curves for blood haemoglobin varieties and/or dye components. Further, an effective extinction coefficient in the tissue is determined via the same mathematical transformation for all small spectral changes in a given light signal.

In a preferred embodiment of the present invention, changes in the spectral emission of a light source operating around a given center wavelength, i.e. variations in the wavelength of the light source are taken into account by utilising the changes in the effective extinction coefficient consistent with the Lambert-Beer theory, by determining the modulation ratio between two light signals for the effective modulation ratio measured in the tissue and the effective modulation ratio according to the Lambert-Beer theory and determining the concentrations of haemoglobin varieties with the aid of the corrected effective extinction coefficients and the effective modulation ratio.

In a preferred embodiment of the present invention, the measurement is calibrated separately for each sensor by storing the determined effective extinction coefficients consistent with the Lambert-Beer theory and/or corrected to correspond to the tissue separately for each light source, preferably for each light element, in a storage device provided in the sensor so that they can be used in the determination of haemoglobin varieties and/or dye components. Furthermore, the function transformations for each light signal pair and/or the center wavelengths are stored in a storage device in the sensor, to be used in the determination of haemoglobin varieties and/or dye components.

In a preferred embodiment of the present invention, to determine a given dyshaemoglobin variety, the proportion of other dyshaemoglobin varieties is set as a constant and the variety to be measured is set as an unknown. In addition, the proportion of other varieties is set to a value corresponding to an invasively measured proportion.

The invention also relates to a sensor for the collection of measurement data through tissue comprised in a patient's blood circulation in non-invasive measurement, said sensor comprising means for connecting the sensor to a measuring apparatus, a light source which transmits a light signal at at least two predetermined center wavelengths and a receiver disposed to receive a light signal transmitted through and/or reflected from the target under measurement. According to the invention, the sensor comprises a storage device for the storage of predetermined sensor-specific data, where the sensor-specific data comprises an effective extinction coefficient for each haemoglobin variety and/or dye component desired, said effective extinction coefficient being characteristic of each light source used. The storage device may be a programmable read-only memory whose contents can be electrically deleted or altered, or a similar memory circuit.

It is further preferable that in the storage device are stored the function transformations and/or center wavelengths for each light signal pair and/or an identifier representing these and/or other corresponding information that indicates the connection between extinction according to the Lambert-Beer theory and extinction measured in tissue, to be used for the determination of haemoglobin varieties and/or dye components.

In a preferred embodiment of the sensor of the present invention, the light source comprises a set of light elements in which the wavelengths to be used, of which at least one is below 660 nm, have been selected from four wavelength ranges as follows: 620–650 nm, 655–665 nm, 680–750 nm and 790–1000 nm. Further, the light elements are thermally anchored on the sensor frame to keep the temperature of the light elements below a specific limit. Moreover, to keep the temperature of the sensor part to be connected to the patient below a specific limit, the sensor comprises a first optic fibre for passing the emitted light to the target under measurement and a second optic fibre for passing the received light to the receiver. In this way, the elements, which tend to get warmed up, can be kept at a distance from the patient.

In a preferred embodiment of the present invention, the sensor comprises a first set of light elements arranged to emit light to a first target and a second set of light elements arranged to emit light to a second target. Further, the first and second sets of light elements have one common wavelength range, which is used for the compensation of variations due to the measuring point. In a preferred case, the measurement signals obtained in the common wavelength range are compared with each other and, based on this comparison, divergences caused by the tissue between measuring points are adjusted.

The sensor may also preferably comprise a set of light filters disposed in conjunction with the receiver to divide the received light into different wavelength ranges. In this manner, light can be transmitted in a wide range of wavelengths, preferably in the range of 600–1000 nm, and the received signal can be filtered into desired wavelength bands.

The sensor may further comprise fixing means for attaching the sensor to the patient, preferably to the patient's ear or finger. It is also possible to attach the sensor to other limbs or organs of the patient.

The present invention also relates to a measuring apparatus for the determination of the relative concentrations or compositions of different kinds of haemoglobin contained in blood, such as oxyhaemoglobin, deoxyhaemoglobin and dyshaemoglobins, and/or dye components, in a non-invasive manner using the light absorption caused by different kinds of haemoglobin and/or dye components. The measuring apparatus of the invention comprises a sensor as described above and a signal processing device for the processing of the signals received. The signal processing device may be a computer, a microprocessor or an application-specific integrated circuit (ASIC) or the like. According to the invention, the apparatus comprises a calculating device and a reader device connected to the calculating device and sensor for reading the data stored in the sensor and transmitting the data to the calculating device. The reader and calculating device may be any electrically controlled component or application known in itself, and it can preferably be incorporated in the signal processing equipment or in the same assemblage with said equipment.

In a preferred embodiment of the present invention, the apparatus is arranged to measure at different wavelengths in accordance with a predetermined time division principle in such manner that the measurement of the shares of certain dye components or haemoglobin varieties is weighted with respect to time so that in a given period of time the apparatus is only measuring in a given part of the entire wavelength range in use. The time division can be effected e.g. using a suitable channel arrangement and channelling device by selecting a given channel at a time for measurement.

In an embodiment of the measuring apparatus of the present invention, the data stored in the sensor includes specific wavelength values for special blood compositions of patients, essential spectral emission information about the light sources used in the sensor, preferably light elements, with respect to different dye components and/or haemoglobin varieties, and/or information about the extinction coefficients according to the Lambert-Beer theory and about the mathematical transformation between these and the extinction coefficients for the tissue. Further, the data stored in the sensor includes information describing the sensor type. Moreover, the measuring apparatus may comprise an identifier device for the identification of sensor type. The identifier device may also be integrated with the reader device.

As compared with prior art, the present invention has the advantage that using the procedure and apparatus of the invention it is possible to eliminate the problems described above relating to prior-art equipment, and above all the invention makes it possible to eliminate the drawbacks and inaccuracies of prior-art methods and apparatus.

Furthermore, the invention presents a new type of calculating method that takes into account the inaccuracies resulting from the scattering and absorption caused by tissue. In addition, the procedure allows compensation of small variations in LED wavelengths.

BRIEF DESCRIPTION OF THE SEVERAL VIEWS OF THE DRAWING

In the following, the invention is described by the aid of a few exemplary embodiments by referring to the attached drawing, in which.

DETAILED DESCRIPTION OF THE INVENTION

Figure 1:
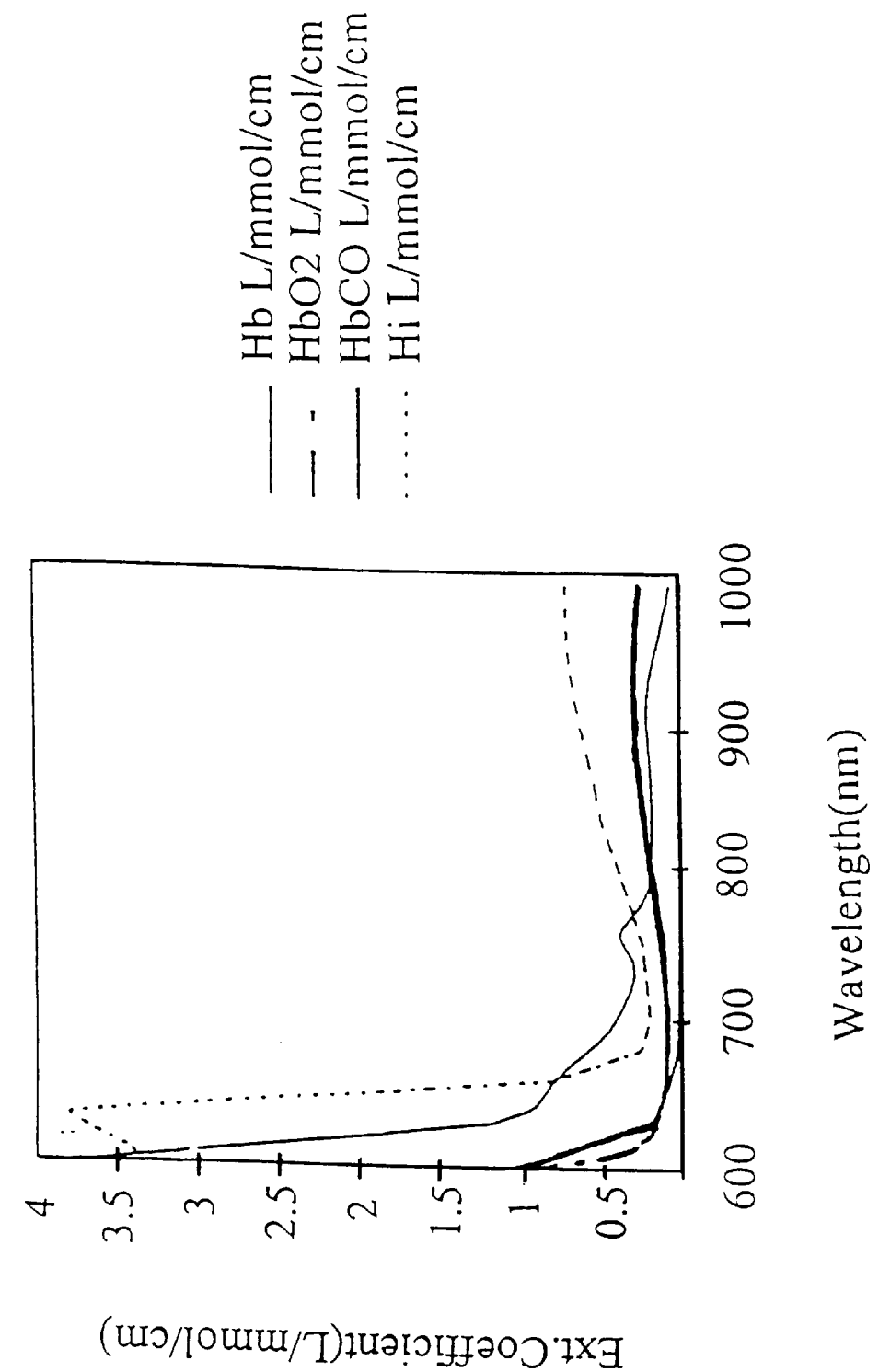
FIG. 1 presents the extinction coefficients of different haemoglobin varieties as functions of wavelength.

FIG. 1 shows the extinction coefficients of different haemoglobin varieties as functions of wavelength. Referring to FIG. 1, certain reasons lying behind the choice of wavelength according to the invention will now be explained. Preferred wavelengths are selected mainly using two criteria: One of the wavelengths, e.g. $\lambda_2$, comprised in the modulation ratio ($\%\text{mod}\lambda_1/\%\text{mod}\lambda_2$) is selected from a range near the isobestic point of the dominating Hb variety or oxyhaemoglobin (HbO2) and the Hb variety whose amount is primarily being measured with the ratio in question, or in general from a range where a change in the relative amount of haemoglobin has only a minor effect on the signal. The other wavelength in the modulation ratio, in this case $\lambda_1$, is so selected that the Hb varieties in question have a large difference between their extinction coefficients at this wavelength. If the isobestic point cannot be used, it is preferable to select the wavelengths so that the difference between the extinction coefficients of the two primary Hb varieties is of opposite sign at the two wavelengths used.

The selection of the primary modulation ratio used in the calculation with four wavelengths from all the ratios possible or all six possible pairs of two wavelengths is also made on two grounds: The modulation ratio must have a high or at least a sufficient sensitivity to a change in the concentration of the Hb variety (Hbxx below) primarily to be measured with this modulation ratio; i.e.

$$\frac{\partial}{\partial (Hbxx)} (\%mod\lambda_1)/(\%mod\lambda_2)$$

is large enough.

On the other hand, the sensitivity of the modulation ratio to sensor specific wavelength variation between the LED components must be low in relation to sensitivity, i.e.

$$\frac{\partial}{\partial \lambda} (\%mod\lambda_1)/(\%mod\lambda_2)$$

is small enough.

Even for as few as four haemoglobin varieties or dye components, simultaneous satisfaction of all criteria is impossible. Selecting the wavelength near the minimum or maximum of the absorption curve reduces the calculation errors caused by variation in the wavelengths of the LEDs. For this reason, the minima and maxima of the absorption curves and in general their flat portions are particularly good choices. If such a flat portion lies near the isobestic point, the wavelength in question is a good reference value, against which the dye differences are formed. In FIG. 1 there are two such ranges: in the range 790–1000 nm, the absorption curves for all Hb varieties are sufficiently insensitive to changes in wavelength, whereas in the range 680–750 nm, only the absorption curve of deoxyhaemoglobin is sensitive to wavelength changes. It is generally advisable to select the wavelengths so that two of the four or more possible wavelengths are the same as in currently used pulse oximeters. When this is the case, all the empirical information available in the case of pulse oximeters is also available when fractional oxygen saturation is measured by means of modulation ratios. The third wavelength range selection is therefore 655–665 nm. Selecting the wavelengths in these three ranges improves the accuracy of fractional oxygen saturation measurement on normal human blood. The wavelength ranges mentioned are also suitable for the determination of HbCO.

As it is not possible to make selection of four wavelength ranges without conflicts, MetHb is treated as a special case. For MetHb measurement, a preferred wavelength range is 625–650 nm. The selection of four different wavelength ranges according to the present invention is: 625–650 nm, 655–665 nm, 680–750 nm and 790–1000 nm. The calculation procedure is then so adjusted that in all situations a maximal accuracy of determination of fractional oxygen saturation is achieved for these wavelength ranges.

Figure 2A:
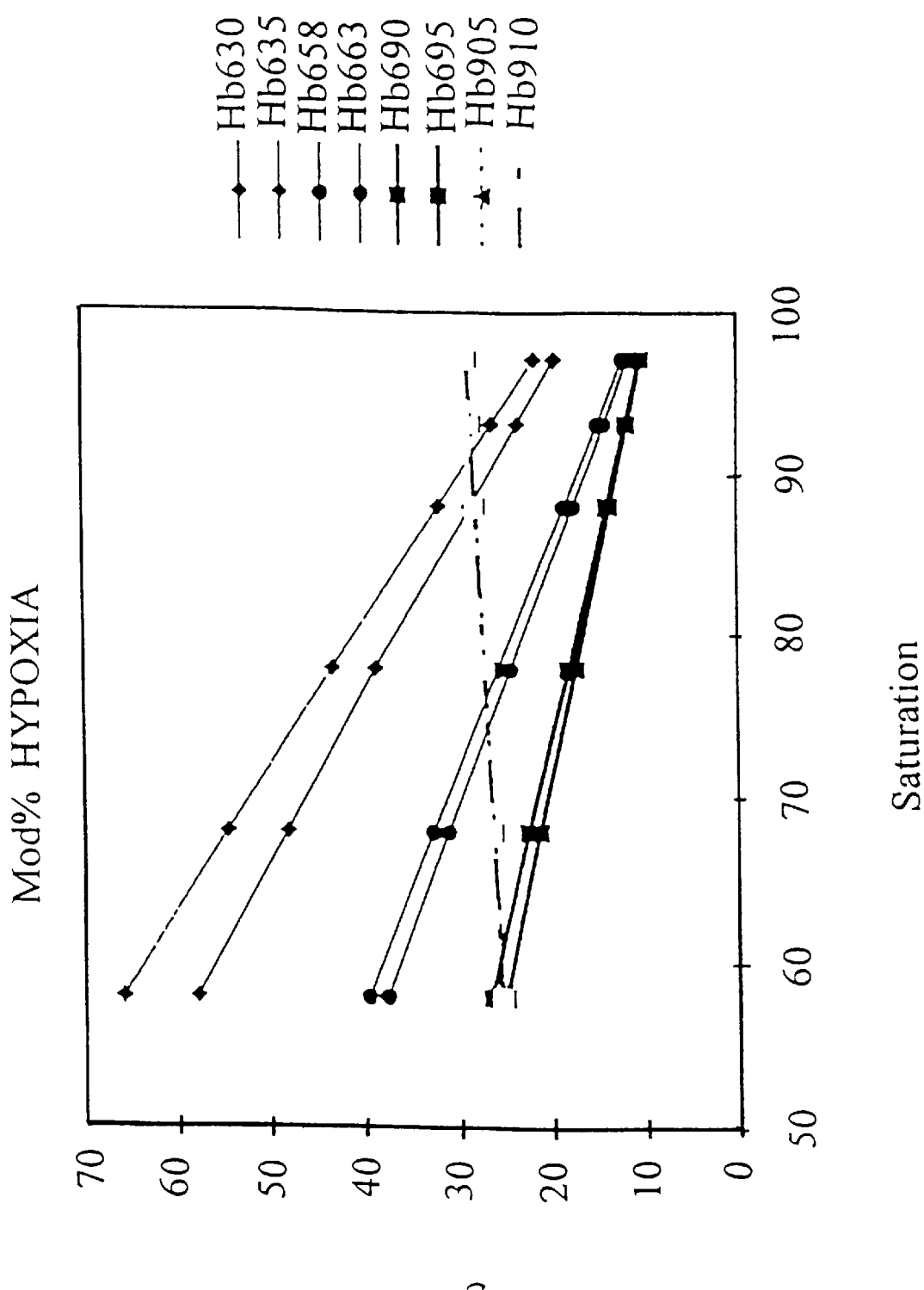
FIGS. 2a–2c represents a preferred wavelength selection according to the present invention.
Figure 2B:
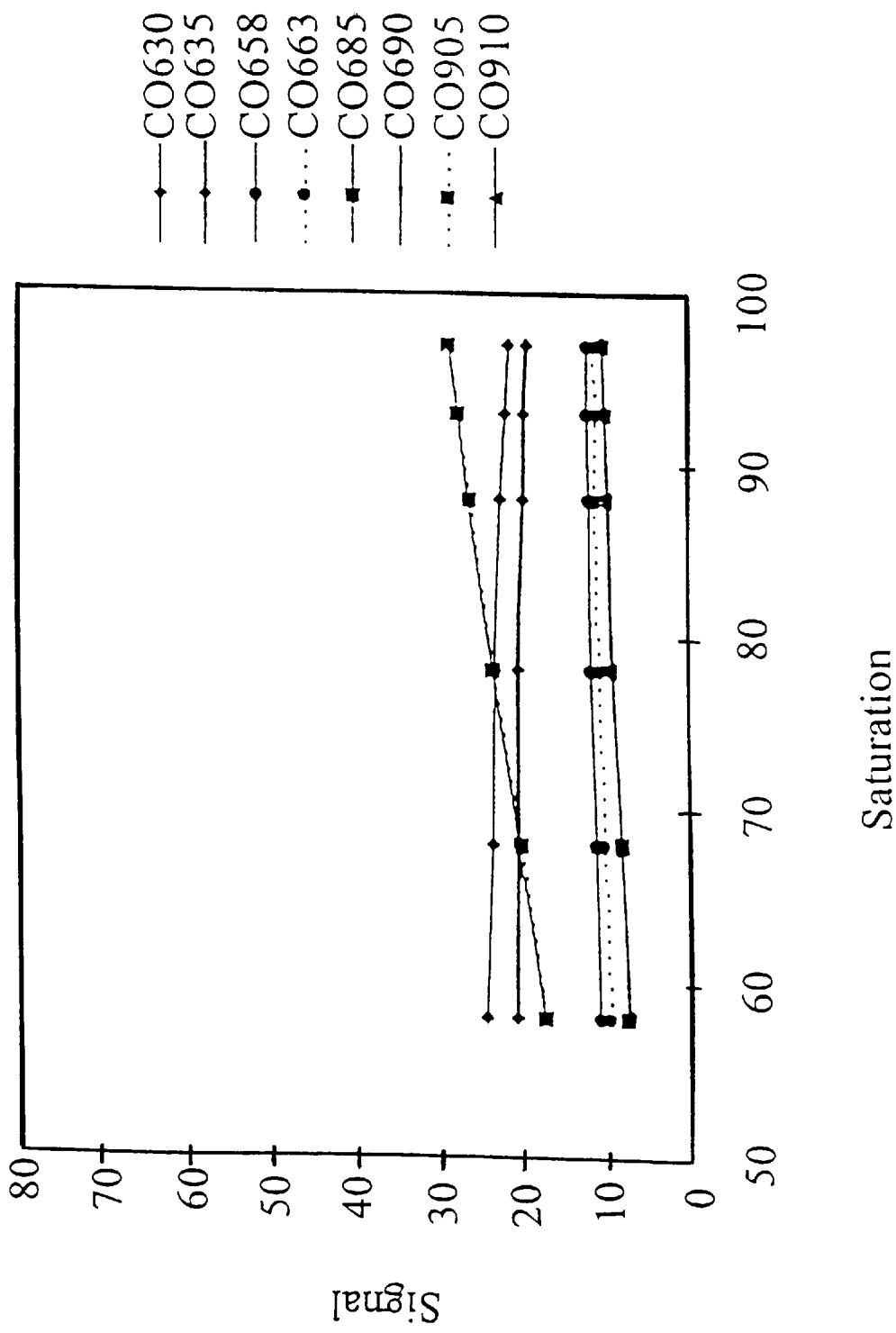
Figure 2C:
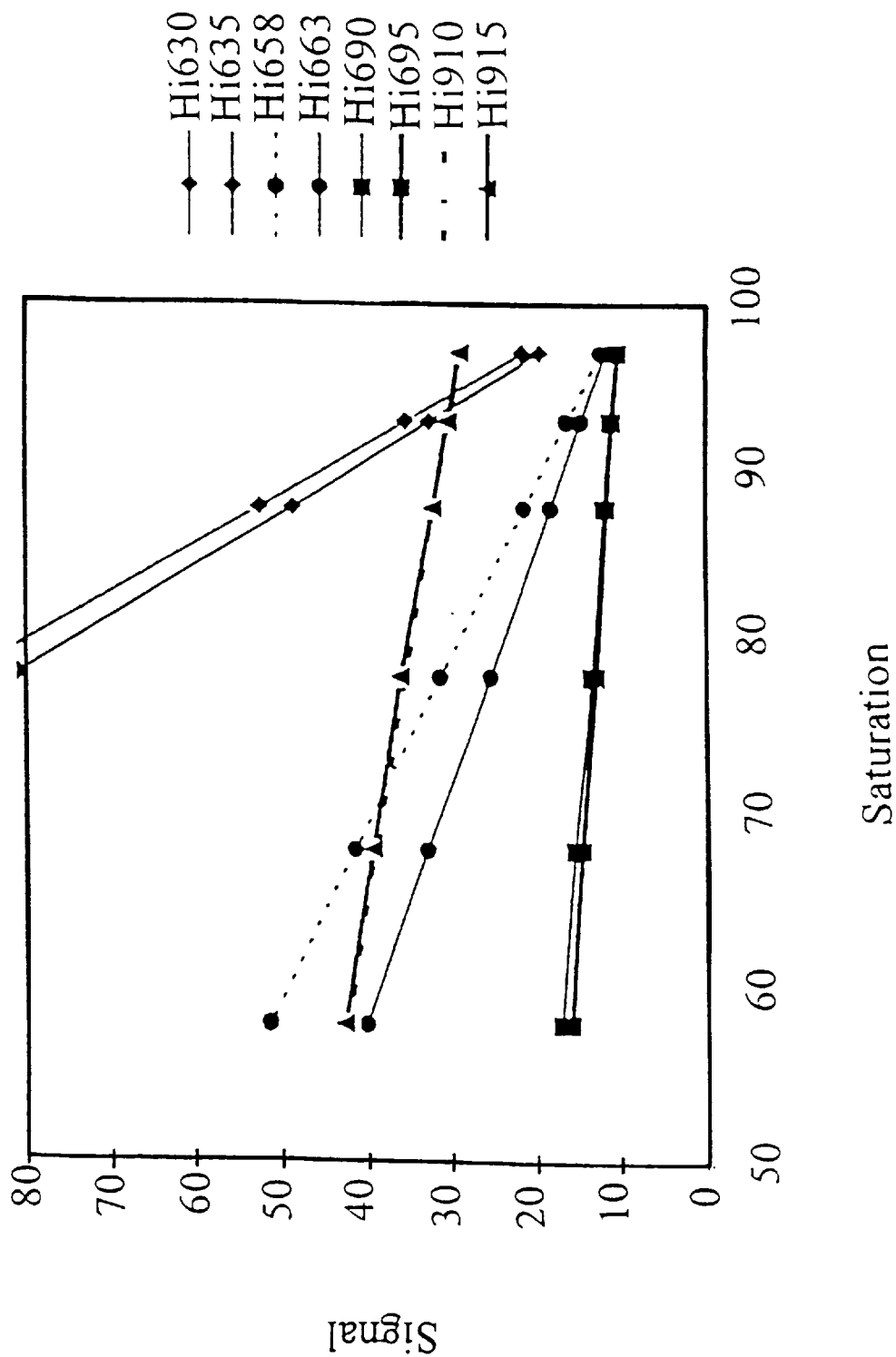

In FIGS. 2a–2c, a preferred optimal wavelength selection is considered using the Lambert-Beer model. Pulse oximeter type modulation signals are presented for three different special situations: 1. Hypoxemia or high Hb level with normal DysHb levels (FIG. 2a), 2. Carboxyhaemoglobimia or high HbCO while other Hb concentrations are normal (FIG. 2b) and 3. Methaemoglobimia or high MetHb level with normal blood composition in other respects (FIG. 2c). In the case presented in FIG. 2, a preferred optimal wavelength selection according to the invention is 900±10 nm, 690±5 nm, 658±5 nm and 630±5 nm. Since the isobestic point between oxyhaemoglobin and carboxyhaemoglobin lies near 645 nm, this is a preferable wavelength for the calculation of the modulation ratio as well. At this wavelength, MetHb can be determined with sufficient accuracy. Another optimal wavelength selection according to the invention is thus 900±10 nm, 690±5 nm, 658±5 nm and 645±5 nm. Table 1 below further illustrates the contradictory nature of the wavelength selection when maximal accuracy of determination is required simultaneously for all different situations. Table 1 shows those wavelengths which should be used in the first place, as well as those which should not be used, for each one of the different descriptions of the patient's condition regarding oxygenation.

TABLE 1

| Special case | Wavelengths that should be used (nm) | Wavelengths that can be used (nm) | Wavelengths that should not be used (nm) |
|---|---|---|---|
| Hypoxemia | 900, 690, 658 | 645 | 630 |
| Carboxyhaemo-globimia | 900, 690 | 658, 645 | 630 |
| Methaemo-globimia | 900, 690, 630 | 645 | 658 |

According to the present invention, the contradictions in the selection of wavelength can be reduced and a better selection accuracy can be achieved by weighting the correct modulation ratios in different ways in each blood oxygenation situation. For instance, in the case of hypoxemia, wavelengths 900 nm, 690 nm and 658 nm and modulation ratios calculated from these are always used and the fractional oxygen saturation is weighted more than the quantities for wavelengths 630 nm or 645 nm. In this case, wavelength 630/645 nm is primarily used to detect the presence of MetHb, but the measurement of the amount of DysHb is effected using other wavelengths. A preferable wavelength pair is 690 nm and 900 nm because both HbCO and MetHb affect this modulation ratio in the same way. When the level of MetHb is found to be rising, the weighting coefficients are altered so that the weighting of wavelength 658 nm is reduced and that of wavelength 630/645 nm is increased. In the case of carboxyhaemoglobin, all wavelengths can be weighted more equally. However, since the absorption coefficients for carboxyhaemoglobin are exceptionally small in the whole range, the HbCO concentration is mainly evident through the fact that carboxyhaemoglobin replaces oxyhaemoglobin. The best wavelength to allow this to be detected is 900 nm, so the modulation ratios for this wavelength must be weighted above the average. A preferred calculation method according to the invention is weighted calculation as described below, which is optimised for the wavelengths used and for the patient's illness condition. The present invention also uses a sensor calibration procedure to be described later on, which allows a good analysing accuracy to be maintained at all wavelengths.

Figure 3:
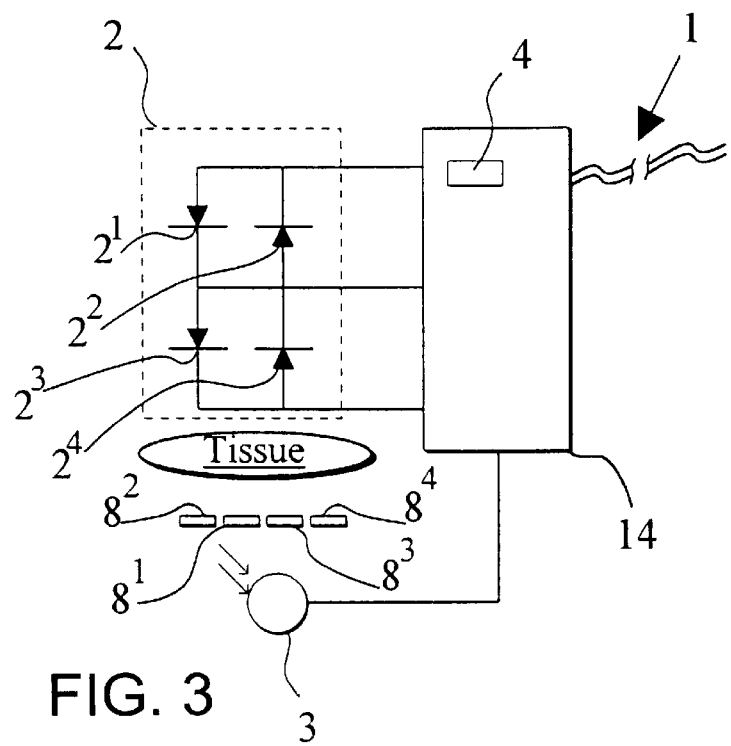
FIG. 3 is a diagram representing a sensor according to the present invention.

FIG. 3 presents a preferred sensor according to the present invention, which is used in the procedure of the present invention for collecting measurement data in a non-invasive measurement through tissue comprised in the patient's blood circulation. The sensor comprises means 1 for connecting the sensor to a measuring apparatus. In this embodiment, the sensor is connected to the measuring apparatus via a cable, known in itself, designed for the transmission of signals. Furthermore, the sensor comprises a light source 2 forming an essential part of it, which emits a light signal at at least two, in the disclosed embodiment, four predetermined medium wavelengths. The light source comprises a number of light elements $2^1, \ldots, 2^4$, each one of which emits light at a selected wavelength different from the others. The sensor also comprises a receiver 3, which typically is a light-sensitive diode or a so-called PIN diode and which is arranged to receive a light signal transmitted through and/or reflected by the target under measurement. The sensor further comprises a storage device 4 for the storage of predetermined sensor-specific data, where the sensor-specific data comprises an extinction coefficient separately determined for each light source and each blood Hb variety and/or dye component that can be measured. The sensor presented in FIG. 3 further comprises a sensor terminal 14, in which the storage device is mounted and to which the light elements $2^1, \ldots, 2^4$ and the receiver 3 are connected. Via the sensor terminal 14, it is possible e.g. to control the sensor by means of the measuring apparatus and to read the data contained in the storage device 4.

The light elements $2^1, \ldots, 2^4$ in FIG. 3 are connected in a bipolar circuit, which uses only three conductors instead of five and is therefore simpler and more advantageous in respect of cable structure. Light elements $2^1, \ldots, 2^2$ and, on the other hand, light elements $2^3, \ldots 2^4$ are connected in reverse directions relative to each other and they are driven by operating current of opposite sign. Such a bipolar control circuit in itself is obvious to the person skilled in the art and is therefore not described here in detail. Generally, the light elements $2^1, \ldots, 2^4$ are small LED chips about $0.3*0.3 \text{ mm}^2$ in size, which are adjusted on a hybrid or circuit board or a corresponding mounting. Surface mounted devices can also be used, but to produce a light source unit as small as possible, chips are a better choice. Further, one light element $2^n$ may consist of two identical light sources (not shown) connected in series. Such a connection is preferable if the LED has an insufficient luminosity when used alone or if the attenuation caused by the tissue at this wavelength is so large that the light transmitted through it is of insufficient intensity.

Figure 4:
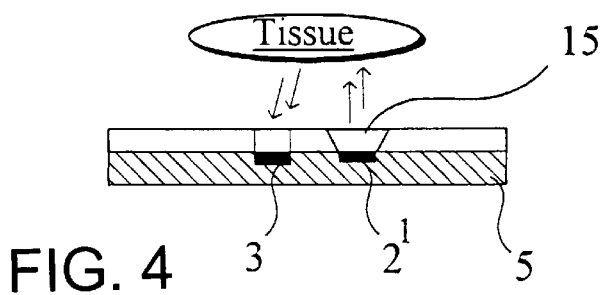
FIG. 4 is a diagram representing a preferred arrangement for mounting a light element according to the present invention.

FIG. 4 presents a particularly advantageous solution that allows the surface temperature of the sensor to be reduced in relation to the conventional structure. In this embodiment of the invention, a light source hybrid $2^1$ is thermally anchored on the sensor frame 5 and its thermal connection to the skin surface is minimised. Such a structure allows a low sensor surface temperature to be maintained even if several light elements are used. Moreover, in the structure presented in FIG. 4, there is between the sensor surface and the light source hybrid a cavity 15 that causes diffuse reflection, thus diffusing and smoothing the light emitted. Therefore, the light emission reaching the skin surface is smoothly spread over a large area, which is an advantage e.g. in regard of the elimination of motional artifacts from the light detector signal. Comprised in the sphere of the present invention are also sensors that may use different wavelength ranges and be intended for some other measurement purpose. Such a sensor may be e.g. one intended for the measurement of blood bilirubin or a given in-vein dye.

FIG. 4 also illustrates a preferred embodiment of the invention, in which the receiver 3 is disposed on the same side relative to the tissue as the light element $2^1$, so that the receiver receives a signal reflected from the tissue. The sensor depicted in FIG. 4 is particularly advantageous in cases where the attenuation caused by the tissue is so strong that the light transmission at all wavelengths is insufficient for the measurement of fractional oxygen saturation in the transmission geometry. In such cases, a reflection sensor as presented in FIG. 4 can be used instead of a series connection of a number of LEDs. Since light transmission decreases especially in the case of short wavelengths, but on the other hand scattering increases at these wavelengths, the advantages of the reflection geometry become manifest via both mechanisms. Thus, the signal produced by the reflection sensor increases in relation to other sensor solutions.

Figure 5:
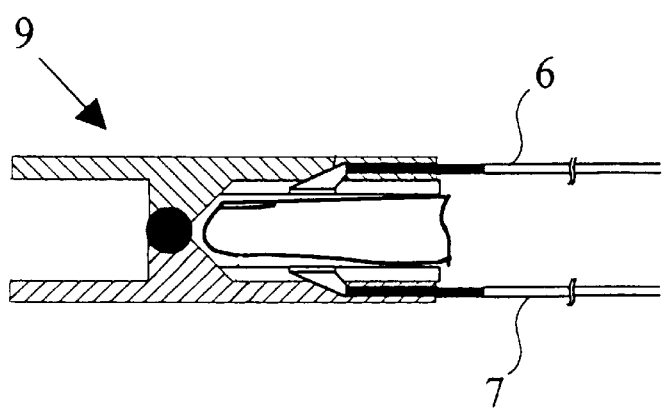
FIG. 5 is a diagram representing a sensor according to the present invention.

FIG. 5 presents a typical finger sensor structure, which comprises a first optic fibre 6 for passing a light signal emitted by a light source (not shown) to the target under measurement and a second optic fibre 7 for passing a light signal transmitted through the tissue to the receiver (not shown). With this sensor structure, too, excessive temperatures against the patient's skin are avoided. In the finger sensor, the fastening device 9 used to attach the sensor components near the target to be measured is a clothes-peg type clamp. Let it be further stated that the solution illustrated by FIG. 5 can be implemented e.g. as an ear sensor or the sensor components can be fastened by means of tape or some other type of separate fixing means.

When a fibre-optic circuit as shown in FIG. 5 is used, the LEDs as well as the detector may be placed inside a patient monitor or a corresponding measuring apparatus, in which case the light is passed via the first optic fibre 6 to the sensor and via the second optic fibre 7 back to the measuring apparatus. In this solution presented in FIG. 5, sensor temperature rise is avoided altogether.

In a preferred embodiment (not shown) of the present invention, two separate sensors are used at different measuring points. One of the sensors is preferably a conventional pulse oximeter sensor. For the other sensor, one common wavelength is selected and used to correct the scaling of the modulation ratios between the sensors, calculated in a crosswise manner. Therefore, in two separate sensors, at least five LEDs must be used instead of four. However, this structure is preferable even in a case where one of the sensors is only used for short periods to measure the dyshaemoglobin level while the other sensor is used continuously e.g. for the measurement of functional oxygen saturation.

Referring again to FIG. 3, the light detector 3 or receiver can be divided into four separate wavelength channels by using light filters. FIG. 3 shows light filters $8^1, \ldots, 8^4$ arranged between the tissue and the receiver 3. Each filter has its own wavelength pass band in accordance with the wavelengths used in each measurement. In a preferred embodiment, the light filters can be electrically controlled so that the passband wavelength can be changed by means of the measuring apparatus. When light filters are used, it is preferable to use a common wide-band light source. In principle, such a light source with sufficient bandwidth may consist of one or more LEDs with a center wavelength of about 680 nm and a bandwidth of about 60–80 nm. In this case, the LED for the near-infrared range may have a wavelength of e.g. 910 nm. Another solution is to use a wide-band halogen or other conventional light source and pass the light via fibre to the oxygen saturation sensor.

Figure 6:
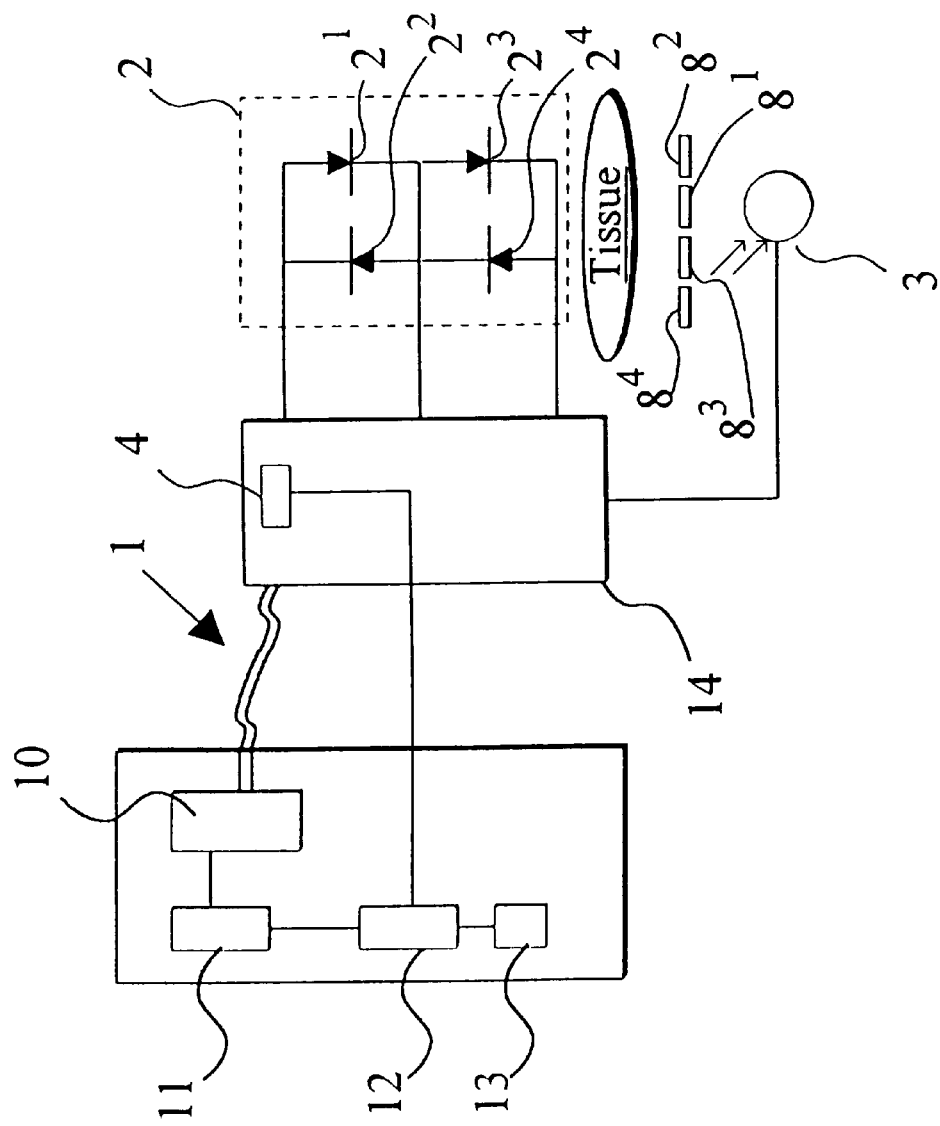
FIG. 6 is a diagram representing a measuring apparatus according to the present invention.

FIG. 6 presents a preferred embodiment of the measuring apparatus of the present invention. The measuring apparatus in FIG. 6 comprises a sensor as described above by referring to FIG. 3, together with a sensor terminal 14. The measuring apparatus preferably comprises at least a signal processing device 10, which may be a microprocessor or a corresponding programmable component known in itself. Further, in this embodiment the light elements $2^1, \ldots, 2^4$ are controlled by two bipolar drive circuits (not shown) controlled by a microprocessor. The radiation emitted by the light elements $2^1, \ldots 2^4$ is passed through the tissue or reflected from it to the light detector 3 of the sensor, from where the signal is passed via the sensor terminal 14 to the current-voltage converter (not shown) of the preamplifier of the apparatus. After this, the signal is amplified in a manner controlled by the microprocessor 10. Let it be further stated that in FIG. 6 the measuring apparatus and sensor are presented in a greatly reduced form because most of the technology used in the measuring apparatus consists of electronics known to the person skilled in the art. The user interface and display functions as well as other general properties of the measuring apparatus are defined via the microprocessor 10. According to the invention, the measuring apparatus presented in FIG. 6 further comprises a calculating device 11, which is programmed to carry out the measuring procedure of the invention with the aid of the sensor. Other essential components in the measuring apparatus are a reader device 12 and an identifier device 13, by means of which the information stored in the memory element 4 of the sensor is read and the sensor type identified. In this context it should also be noted that with modern technology even a hardware implementation is possible in which all the above-mentioned components, i.e. the signal processing device 10, calculating device 11, reader device 12 and identifier device 13, are programmed into a single application-specific integrated circuit (ASIC).

A preferred embodiment of the present invention is one in which the measuring time in the embodiment presented in FIG. 6 is flexibly divided between the channels. In this case, e.g. most of the time would be spent on measuring the fractional oxygen saturation while a clearly shorter time is reserved for dyshaemoglobin measurement or the dyshaemoglobin level is only determined when necessary. The time division used in the measurement may be a fixed division or it can be flexibly changed as required in each situation.

The theory of pulse oximetry is generally presented as being based on the Lambert-Beer law. According to the theory, light transmission through the tissue at each wavelength is exponentially dependent on the absorbance of the tissue. This theory is generally accepted and established in pulse oximetry. Omitting details, the theory is generalised for four different wavelengths in the matrix format described above, as follows:

$$\begin{pmatrix} \%mod1 \\ \%mod2 \\ \ldots \\ \%mod3 \end{pmatrix}^* = C^*(T) \begin{pmatrix} \varepsilon_{11} & \ldots & \varepsilon_{1j} \\ \varepsilon_{21} & \ldots & \varepsilon_{2j} \\ & \ldots & \\ \varepsilon_{il} & \ldots & \varepsilon_{ij} \end{pmatrix}_{ij} \cdot \begin{pmatrix} HbX_1 \\ HbX_2 \\ \ldots \\ HbX_j \end{pmatrix} \quad (1)$$

where %mod i is the modulation percentage for light transmission as measured at wavelength i, i.e. the proportion of light transmission varying at heartbeat frequency as a percentage of the total light transmission, the ij-element of the $\varepsilon$-matrix is the extinction coefficient of the haemoglobin component j of arterial blood for wavelength i and the haemoglobin components in percentages are placed in the vertical vector $(HbX_1, HbX_2, \ldots, HbX_j)$ in this order j. Thus, the horizontal lines of the $\varepsilon$-matrix are the extinction coefficients of a given wavelength for different Hb varieties. The constant C determines the units on the left side of the equation.

In the above system of equations it has been assumed that the modulation percentage is small (<10%). If this is not the case, instead of %mod i the exact theoretic form is used:

$$\% \bmod i \leftarrow \ln(1 \pm \% \bmod i/100\%)*100\%$$

The modulation percentages are the basic signals of the pulse oximeter, so in the Lambert-Beer theory it should be possible to calculate the concentrations of different Hb varieties directly by using a matrix reverse to the $\varepsilon$-matrix. However, in practice this system of equations is not linear. As stated before, the divergences between theory and practice are due to the fact that the actual extinction coefficients $\varepsilon'$ are also dependent on the scattering of light caused by the tissue and blood and on the combined effect of absorption and scattering. The corrections are larger the larger is the proportion of the attenuation caused by absorption and scattering. The Lambert-Beer law assumes that the scattering of light and the non-homogeneity of tissue are not taken into account. In practice, therefore, in non-invasive measurement the elements $\varepsilon_{ij}$ of the $\varepsilon$-matrix differ from the extinction coefficients $\varepsilon'_{ij}$ of real blood. This correlation between the actual and theoretical extinction matrices can be represented by a transformation T that depends on the total absorption and scattering at the wavelengths used in measurement. This relationship can be presented in the following form:

$$\begin{pmatrix} \varepsilon_{11} & \ldots & \varepsilon_{1j} \\ \varepsilon_{21} & \ldots & \varepsilon_{24} \\ & \ldots & \\ \varepsilon_{il} & \ldots & \varepsilon_{ij} \end{pmatrix}^* = (T) \begin{pmatrix} \varepsilon_{11} & \ldots & \varepsilon_{1j} \\ \varepsilon_{21} & \ldots & \varepsilon_{24} \\ & \ldots & \\ \varepsilon_{il} & \ldots & \varepsilon_{ij} \end{pmatrix}_{ij} \quad (2)$$

The * sign at the top edge of the matrix means that the elements of the matrix are $\varepsilon'_{ij}$.

Since the total absorption is the sum of the extinction coefficients weighted by the haemoglobin proportions, the transformation T is dependent on the haemoglobin concentrations themselves, or $$(T)=(T)(HbX_1, HbX_2, HbX_3, \ldots, HbX_j)$$

In multi-component analysis of blood composition, the divergence between theory and practical measurements has significant consequences, which are disregarded e.g. in patent application EP 0 524 083 A1. First, the system of equations (1) is not linear, i.e. it cannot be solved by using a reverse matrix. Second, any Hb variety and change in its concentration also affects the actual extinction coefficients of other Hb varieties. For this reason, the system of equations (1) must be solved for all Hb varieties present in blood, and the fairly strongly absorbing MetHb variety cannot be excluded from the analysis.

In the following, referring to FIG. 7, which depicts the correlation of theoretic and empiric oxygen saturation as functions of the ratio (R/IR) of the modulation percentages determined at wavelengths 660 nm (R) and 940 nm (IR), it will be demonstrated how the system of equations (1) is solved with the aid of the modulation percentage ratios for several Hb varieties, i.e. HbO2, Hb, HbCO, MetHb and Hbx, where Hbx is a haemoglobin component that appears in the patient's blood in a special situation, e.g. nitrosylhaemoglobin HbNO or sulphohaemoglobin HbS. In principle, Hbx may represent any blood dye component, such as an artificial dye.

Figure 7:
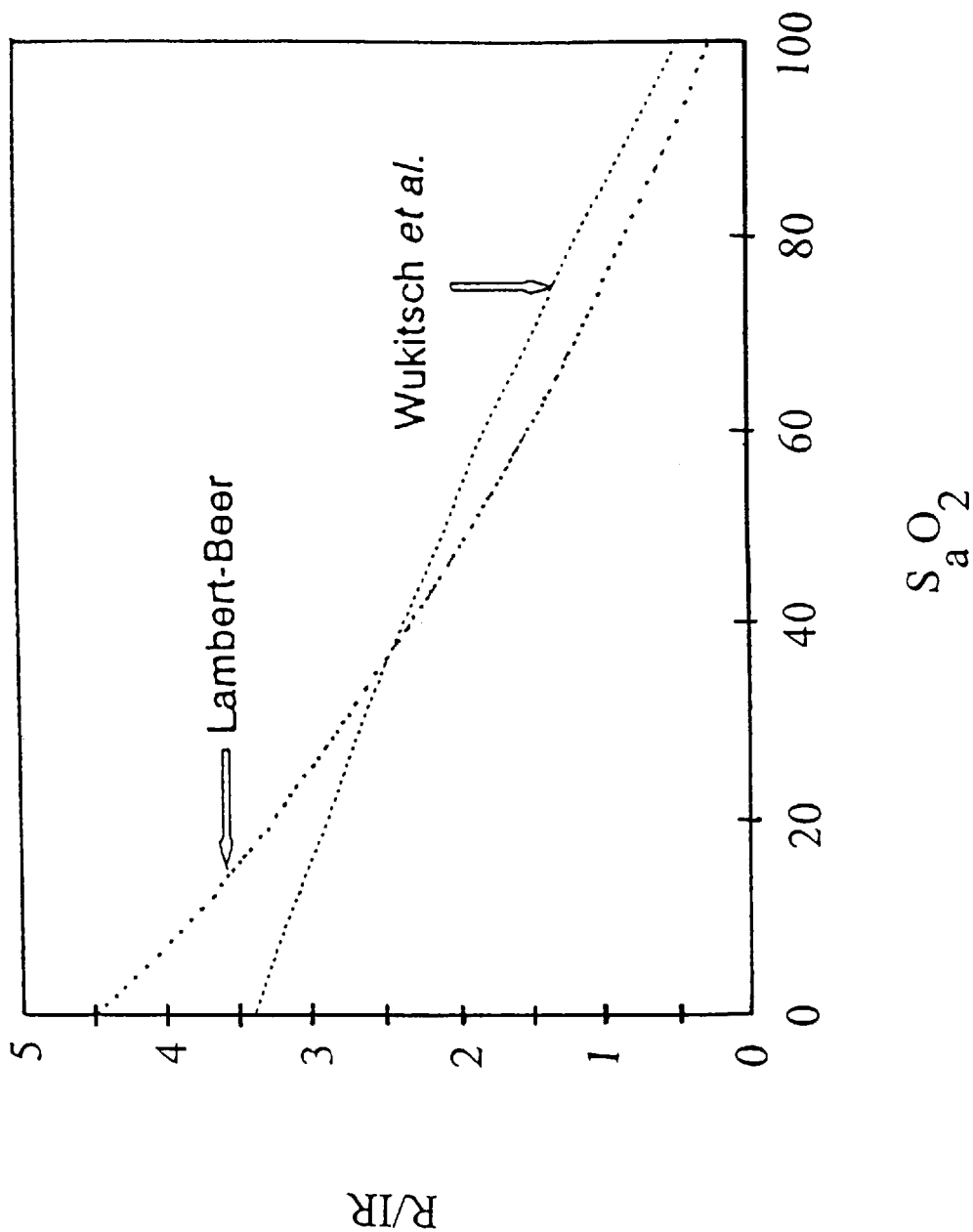
FIG. 7 illustrates the correlation of theoretic and empirical oxygen saturation as functions of the ratio (R/IR) of modulation percentages determined at wavelengths 660 nm (R) and 940 nm (IR).

In FIG. 7, the significance of the matrix transformation (2) is that the transformation serves to transfer the theoretical Lambert-Beer curve onto the empirical curve (in the figure, Wukitsch et al). This can be effected via a function conversion that changes the numeric values on the R/IR axis in the desired (non-linear) manner. With four different wavelengths, a corresponding correlation between the theoretical and empirical modulation ratios and the oxygen saturation level is obtained for each one of the six different wavelength pairs. The transformation T contains the information needed for the transfer of all these pairs of curves, and conversely, the transfer of the curve pairs determines the transformation T. Below is a description of how this kind of transformation functions in multi-component analysis of Hb varieties with a plurality of different wavelengths and a plurality of different haemoglobin components.

The description is limited to the use of four different wavelengths. However, under certain assumptions, the procedure can be used to analyse more than four Hb varieties with sufficient accuracy.

In the analysing procedure of the invention, the total extinction coefficient of dyshaemoglobins at wavelength i is written as:

$$\varepsilon_{i3} = \frac{MetHb}{DysHb} * \varepsilon_{i3}(MetHb) + \frac{HbCO}{DysHb} * \varepsilon_{i3}(HbCO) + \frac{Hbx}{DysHb} * \varepsilon_{i3}(HbX) \quad (3)$$

where $$DysHb = MetHb + HbCO + HbX \quad (4)$$

and HbX is a third dyshaemoglobin variety. In its general representation HbX can also be interpreted as an artificial dye concentration in blood.

With four different wavelengths, the unknown system of equations can be written in the form:

$$\begin{pmatrix} \%mod1 \\ \%mod2 \\ \%mod3 \\ \%mod4 \end{pmatrix} = C^* \begin{pmatrix} \varepsilon_{11} & \varepsilon_{12} & \varepsilon_{13} \\ \varepsilon_{21} & \varepsilon_{22} & \varepsilon_{23} \\ \varepsilon_{31} & \varepsilon_{32} & \varepsilon_{33} \\ \varepsilon_{41} & \varepsilon_{42} & \varepsilon_{43} \end{pmatrix} \cdot \begin{pmatrix} HbO2 \\ 1 - HbO_2 - DysHb \\ DysHb \end{pmatrix} \quad (5)$$

where the $\epsilon$-matrix is in accordance with the Lambert-Beer theory and contains the extinction coefficients documented for blood in literature. The modulation percentages predicted by the theory are thus in the vertical %mod i vector. C again represents the transformation of the units. The concentrations of different Hb varieties are presented as proportional shares.

The experimentally measured modulation percentages are:

$$\begin{pmatrix} \%mod1 \\ \%mod2 \\ \%mod3 \\ \%mod4 \end{pmatrix}^* = C^*(T) \begin{pmatrix} \varepsilon_{11} & \varepsilon_{12} & \varepsilon_{13} \\ \varepsilon_{21} & \varepsilon_{22} & \varepsilon_{23} \\ \varepsilon_{31} & \varepsilon_{32} & \varepsilon_{33} \\ \varepsilon_{41} & \varepsilon_{42} & \varepsilon_{43} \end{pmatrix} \cdot \begin{pmatrix} HbO2 \\ 1 - HbO_2 - DysHb \\ DysHb \end{pmatrix} \quad (6)$$

By comparing equations 5 and 6, one observes that $$\begin{pmatrix} \%mod1 \\ \%mod2 \\ \%mod3 \\ \%mod4 \end{pmatrix} = (T^{-1}) \begin{pmatrix} \%mod1 \\ \%mod2 \\ \%mod3 \\ \%mod4 \end{pmatrix}^* \quad (7)$$

It can be observed at this point that the transformation T is neither linear nor e.g. a matrix multiplication, but it does have an unambiguous inverse transformation $T^{-1}$. We shall now calculate a representation of this transformation.

Equation (5) is divided into modulation ratios as follows:

$$\frac{\% \ mod \ k}{\% \ mod \ 1} = \frac{\varepsilon_{k1} * HbO2 + \varepsilon_{k2} * (1 - HbO2 - DysHb) + \varepsilon_{k3} * DysHb}{\varepsilon_{11} * HbO2 + \varepsilon_{12} * (1 - HbO2 - DysHb) + \varepsilon_{13} * DysHb} \quad (8)$$

where k,l=1, 2, 3, 4 and k #1. In the case of four wavelengths, this division can be made in six different ways, i.e. there will be six expressions (8).

Let us write $[(\%mod \ k)/(\%mod \ l)] = Z$ and solve each equation (8) for HbO2:

$$HbO2 = \frac{(1 - DysHb) * (\varepsilon_{k2} - Z * \varepsilon_{12}) + DysHb * (\varepsilon_{k3} - Z * \varepsilon_{13})}{Z * (\varepsilon_{k1} - \varepsilon_{11}) - (\varepsilon_{k2} - \varepsilon_{12})} \quad (9)$$

The theoretical modulation ratio Z can be expressed using an experimentally measured modulation ratio Z' so that $$Z = f_{kl}(Z') \quad (10)$$

which determines the transformation inv (T): Z'→Z. The experimentally correct fractional oxygen saturation is obtained from equation (9) by substituting formula (10) for Z. Consequently, when the wavelengths are 660 nm and 940 nm, function f (660,940) transfers the experimentally measured curve in FIG. 7 onto the Lambert-Beer curve by changing the numeric values on the vertical axis in the manner determined by function f(660,940). Function f depends on the total absorption and scattering appearing at wavelengths k and l, but no longer on different Hb varieties. Thus, function f can be found e.g. via hypoxemia tests with normal HbCO and MetHb concentrations. This makes the calibration of fractional saturation measurement considerably easier. Function f is known via the calibration data for conventional pulse oximeter measurement at wavelengths R=660 nm and IR=900 nm (or 940 nm). If the representations of transformation inv(T) are designated e.g. at wavelengths 630 nm, 690 nm and 900 nm as follows:

$$R = f \ 660, 900(R')$$
$$Q = f \ 660, 690(Q')$$
$$P = f \ 630, 690(P') \quad \Leftrightarrow \quad \begin{pmatrix} \%mod1 \\ \%mod2 \\ \%mod3 \\ \%mod4 \end{pmatrix} = (T^{-1}) \begin{pmatrix} \%mod1 \\ \%mod2 \\ \%mod3 \\ \%mod4 \end{pmatrix}^*$$
$$S = f \ 690, 900(S')$$
$$T = f \ 630, 660(T')$$
$$U = f \ 630, 900(U')$$

then all functions f can be determined by changing the concentration of one Hb variety and therefore the total absorption for the wavelength in question.

Representations R'–R, Q'–Q, P'–P, S'–S, T'–T and U'–U being known, equations (3) and (4) are solved and the fractional saturation level is solved for 3–6 modulation ratios from the system of equations (9) iteratively so that the fractional oxygen saturation level HbO2, total concentration of dyshaemoglobin DysHb and the composition of dyshaemoglobin varieties can be determined in a compatible manner. The calculation may include verification of the result by checking it against the condition built into the equations that the sum of all Hb varieties is 100%. The iteration process can be accelerated using clinical information about the patient's condition. Typically, only one DysHb variety in the patient's blood has an increased value. Moreover, the amount of dyshaemoglobin changes slowly with time, so equations (3) and (4) need not necessarily be used in real-time calculation of the fractional oxygen saturation level. These equations thus have a greater importance in the identification of dyshaemoglobin varieties.

Above, the way in which multi-component analysis of haemoglobin composition of blood can be implemented has been described. Next, we shall discuss the question of how the concentration of dyshaemoglobin can be identified. After that there follows a discussion of how the sensor calibration data are saved.

In clinical measurement of fractional oxygen saturation, the dyshaemoglobin variety to be monitored is generally known beforehand. It is generally also known that the concentrations of other dyshaemoglobin varieties are normal and remain unchanged in the planned treatment. In such a situation, the user may input the dyshaemoglobin variety of primary interest into the apparatus. In this case, the non-interesting dyshaemoglobin concentrations are set as normal parameters in expressions (3) and (4) while the dyshaemoglobin variety of primary interest is set as an unknown parameter. In principle, the user may also make haemoglobin values measured from a blood sample available to the apparatus. The apparatus performs the calculation using oxyhaemoglobin (HbO2), deoxyhaemoglobin (Hb) and the dyshaemoglobin variety of primary interest as unknown variables while the amount of other dyshaemoglobin varieties is taken to be constant.

For reasons of user friendliness, it is generally required that it should be possible to "measure" the dyshaemoglobin variety in the same way as the amount of oxyhaemoglobin. In this case, the dyshaemoglobin composition is not known in advance, and the effects of treatment administered to the patient are not known, either. In principle, the normal composition of human blood, which contains four haemoglobin varieties, can be analysed with four different wavelengths. In the blood of a person who is critically ill, other HbX varieties or other dyes may exist in consequence of treatment or medication. The existence of these may be identified by stipulating that the HbO2 value calculated via iteration from six different modulation ratios should fall within certain predetermined limits of variation. An additional stipulation that may be applied is the assumption included in the equations that the sum of haemoglobin varieties should be 100%. Identification of a divergent HbX variety or dye is effected when the iteration result is not consistent. If the result of iterative calculation indicates an increased MetHb value and the patient is having NO-treatment, the HbX variety is assumed to be nitrosyl-haemoglobin HbNO. The extinction coefficient of this is added to expressions (3) and (4). The HbCO in the expressions is set to the normal level or about 1%. If the next iterative calculation yields a substantially better consistency, HbNO is identified. If in normal iterative calculation no increased MetHb or HbCO values are observed but the accuracy of iteration is low, then a check is made to verify whether any other pre-programmed Hb varieties or dyes exist. If the iterative calculation yields a substantially better result, then the haemoglobin variety or dye in question is identified.

Another advantage provided by the calculation method described above is that changes in the sensor LED wavelengths can be easily and simply taken into account in the calculation of fractional saturation. The sensor calibration process comprises the following steps:

1. The wavelengths and spectral emission of the sensor LEDs are measured.
2. For the absorption curves of Hb varieties documented in the Lambert-Beer theory or in literature, an effective extinction coefficient is calculated for the wavelength of each LED, taking into account the medium wavelength and spectral line width of the LED. The receiver sensitivity curve can also be included in this process.
3. The extinction coefficients $\epsilon_{ij}$ are stored separately e.g. in matrix format for all light elements.
4. The matrix of the extinction coefficients is stored in a storage device, such as an EEPROM, provided in the sensor.
5. Transformations of the theoretical extinction matrix and of an empirical matrix are stored in the same EEPROM as functions R, Q, P, S, T, and U. These functions are used in the procedure in the manner described above.
6. The sensor type, i.e. optionally MetHb sensor, CO sensor, etc., is stored in the EEPROM.
7. Data relating to the manufacture and guarantee of the sensor and other corresponding data are stored in the EEPROM.

Therefore, the sensor of the present invention provides a great advantage because the measuring apparatus can read the contents of the EEPROM and use the calibration data in the calculation of fractional saturation.

The invention is not limited to the examples of its embodiments described above, but instead many variations are possible within the framework of the inventive idea defined by the claims.

We claim:

1. A method for non-invasively determining the amount of a light absorbing substance in the blood of a subject, the blood having at least two light absorbing substances, said method comprising the steps of:

(A) applying light of a first wavelength to tissue of the subject containing blood to obtain a first transmitted light quantity, the first transmitted light quantity having a pulsatile component and a non-pulsatile component;

(B) applying light of a second wavelength to tissue of the subject containing blood to obtain a second transmitted light quantity, the second transmitted light quantity having a pulsatile component and a non-pulsatile component;

(C) ratioing the pulsatile component of the first transmitted light quantity to the total first transmitted light quantity and ratioing the pulsatile component of the second light quantity to the total second transmitted light quantity to obtain first and second percentage modulation quantities (% mod 1, 2 . . . );

(D) ratioing the first and second percentage modulation quantities (% mod 1, 2 . . . ) to obtain a modulation ratio quantity (Z');

(E) formulating substance concentration determining equations (Eq 8, 9) for wavelengths corresponding to the first and second light wavelengths;

(F) altering one of a modulation ratio term (Z', Z) or extinction coefficient terms ($\epsilon'$, $\epsilon$) in the equations in accordance with the percentage modulation quantities to account for the application of the light of the first and second wavelengths to the tissue as well as the blood of the subject;

(G) solving the equations for at least one selected substance present in the blood; and (H) determining, from the solution of the equations, the amount of the selected substance in the blood.

2. The method according to claim 1, wherein step (F) is further defined as applying a function (f) to the modulation ratio quantity (Z') obtained from the transmitted light modulation percentage quantities to obtain a modulation term (Z) for use in the solution of equations formulated according to the Lambert-Beer law.

3. The method according to claim 1, wherein step (F) is further defined as applying an extinction coefficient transform (T) to substance extinction coefficients ($\epsilon_{ij}$) obtained in accordance with the Lambert-Beer law to provide haemoglobin extinction coefficients ($\epsilon'_{ij}$) for blood in tissues and wherein step (G) is further defined as solving the equations using the modulation ratio quantity term (Z') obtained from the transmitted light modulation percentage quantities.

4. The method according to claim 1, further defined as a method for determining the relative amount of a given form of haemoglobin in the blood of the subject, the blood having at least two forms of haemoglobin, wherein step (G) is further defined as solving the equations for at least one selected form of haemoglobin in the blood, and wherein step (H) is further defined as determining the relative amount of the given form of haemoglobin in the blood.

5. The method according to claim 4, wherein step (G) is further defined as solving the equations for all haemoglobin forms present in the blood.

6. The method according to claim 4, further including the step of iteratively solving the equations to determine the relative amount of a selected given form of haemoglobin.

7. The method according to claim 4, further including the steps of iteratively solving the equations and as identifying a selected given form of haemoglobin from the results of the iterative solutions.

8. The method according to claim 4, further defined as iteratively solving the equations for a given form of haemaglobin present in the blood while formulating the equations in accordance with the assumption that the amounts of one or more other forms of haemoglobin in the blood remain constant.

9. The method according to claim 4, further including the step of iteratively solving the equations for a given form of haemoglobin to determine changes over time in the amount of the given form of haemoglobin.

10. The method according to claim 1 wherein the method includes the steps of:

applying light of four different wavelengths to the tissue of the subject to provide four transmitted light quantities;

step (C) is further defined as ratioing the pulsatile and total transmitted light quantities of each of the wavelengths to obtain four percentage modulation quantities;

step (D) is further defined as ratioing the four percentage modulation quantities to obtain a plurality of modulation ratio quantities;

step (E) is further defined as formulating equations for the four different wavelengths; and step (F) is further defined as altering the modulation ratio term (Z', Z) or extinction coefficient terms ($\epsilon'$, $\epsilon$) to account for the application of light of the four wavelengths to the tissue, as well as the blood of the subject.

11. The method according to claim 10, further including the step of iteratively solving the equations and wherein one or more modulation ratios derived from selected wavelengths is/are weighted in the iterative solution of the equations.

12. The method according to claim 10, further defined as a method for determining the relative amount of a given form of haemoglobin in the blood of the subject, the blood having at least two forms of haemoglobin, wherein step (G) is further defined as solving the equation for at least one selected form of haemoglobin in the blood, and wherein step (H) is further defined as determining the relative amount of the given form of haemoglobin in the blood.

13. The method according to claim 4, or claim 12, further defined as including the step of selecting one of said wavelengths so that there is a large difference between the extinction coefficients of selected forms of haemoglobin at the one wavelength and selecting another wavelength to be at or near the isobestic point of the extinction coefficients of the selected forms of haemoglobin.

14. The method according to claim 4, or claim 12, further defined as including the step of selecting one of said wavelengths so that there is a large difference of one sign between the extinction coefficients of selected forms of haemoglobin at the one wavelength and selecting another wavelength so that there is a large difference of the opposite sign between the extinction coefficients of the selected forms of haemoglobin at the another wavelength.

15. The method according to claim 4, or claim 12, wherein the wavelengths are selected in a range of 600 nm to 1000 nm.

16. The method according to claim 15, wherein the wavelengths are selected from the following ranges: 620–650; 655–665; 680–750; and 790–1000 nm.

17. The method according to claim 16, wherein the wavelengths are selected as follows: 645; 658; 690; and 900 nm.

18. A method according to claim 16, wherein the wavelengths are selected as follows: 632, 658, 690, and 900 nm.

19. A method according to claim 15, wherein at least one of the wavelengths is below 660 nm.

20. A method according to claim 15, further including the step of iteratively solving the equations and wherein modulation ratio quantities derived from wavelengths of 660 nm, 690 nm, and 900 nm are weighted with respect to modulation ratio quantities derived from wavelengths in a range of 620–650 nm.

21. A method according to claim 15, further defined as determining the relative amount of at least one of methaemoglobin and carboxyhaemoglobin in the blood and as using light having a wavelength in a range of 620–650 nm.

22. A method according to claim 4, or 12 further defined as determining the relative amount of oxyhaemoglobin or deoxyhaemoglobin in the blood.

23. A method according to claim 4, or 12 further defined as a method for determining the relative amount of a plurality of forms of haemoglobin and as including the step of applying light having a plurality of different wavelengths, the number of different wavelengths corresponding to the number of forms of haemoglobin, the relative amounts of which are to be determined.

24. A method according to claim 23, further defined as a method for determining the relative amount of one or more of oxyhaemoglobin, deoxyhaemoglobin, and dyshaemoglobins in the blood.

25. The method according to claim 10, wherein the wavelengths are selected to optimize the determination of a given form of haemoglobin.

26. A method according to claim 1, wherein steps (A) and (B) are further defined as applying light to substantially the same blood containing tissue in both steps.

27. A method according to claim 1, wherein the modulation ratio quantity and extinction coefficient terms in the equation are altered responsive to small spectral changes in the wavelengths of the light.

28. A method according to claim 1, further defined as carrying out a calibration procedure and including the steps of obtaining modulation ratio quantities (Z') from the blood of the subject for the first and second wavelengths; obtaining extinction coefficients and modulation ratio quantities (Z) under Lambert-Beer law conditions for the first and second wavelengths for blood having the same properties as the subject's blood; comparing the modulation ratio quantities (Z, Z'); and using data from the comparison to calibrate the determination method.

29. A method according to claim 1, wherein steps (A) and (B) are further defined as passing light through tissue of the subject.

30. A method according to claim 1, wherein steps (A) and (B) are further defined as reflecting light off the tissue of the subject.

31. A sensor for use in determining the amount of one or more light absorbing substances in the blood of a subject, said sensor comprising:
- a light source emitting light for application to blood containing tissue of the subject, the emitted light of said source having at least two predetermined center wavelengths;
- a receiver receiving light from the tissue;
- a data storage device storing extinction coefficient data, the stored data including extinction coefficients separately determined for each predetermined center wavelength and substance; and
- output means for providing output signals from said sensor relating to characteristics of the light received by said receiver and the extinction coefficients stored in said data storage device.

32. A sensor according to claim 31, wherein said storage device is further defined as storing functions which are applied to signal quantities resulting from the light received by said receiver to obtain output signal quantities suitable for use in the solution of equations formulated according to the Lambert-Beer law.

33. A sensor according to claim 31, wherein said data storage device is further defined as storing an extinction coefficient transform appliable to extinction coefficients obtained in accordance with the Lambert-Beer law to provide substance extinction coefficients for blood in tissue.

34. A sensor according to in claim 31, wherein said storage device is further defined as storing sensor identification information.

35. A sensor according to claim 31, further defined as a sensor for determining the relative amount of one or more forms of haemoglobin in the blood of the subject.

36. A sensor according to claim 35, wherein said light source comprises a plurality of light emitting elements emitting light having predetermined center wavelengths, at least one of which is below 660 nm, said light emitting elements emitting light in the following wavelength ranges; 620–650 nm, 655–665 nm, 680–750 nm, and 790–1000 nm.

37. A sensor according to claim 31 further including filter means in the light path between said light source and said receiver for providing light having said at least two predetermined center wavelengths.

38. A sensor according to claim 35, including filter means in the light path between said light source and said light receiver and wherein said filter means provides light of a plurality of predetermined center wavelengths, at least one of which is below 660 nm, said filter means providing light in the following wavelength ranges; 620–650 mn, 655–665 nm, 680–750 nm, and 790–1000 nm.

39. A sensor according to claim 31, wherein said light source comprises a first set of light emitting elements and a second set of light emitting elements, and wherein said first and second sets of light emitting elements emit light in one common wavelength range.

40. A sensor according to claim 31, wherein said light source and said receiver are arranged so that said receiver receives light transmitted through the blood containing tissue.

41. A sensor according to claim 31, wherein said light source and said receiver are arranged so that said receiver receives light reflected from the blood containing tissue.

42. A sensor according to claim 31, wherein said light source produces heat and is mounted on a heat sink for maintaining the temperature of said light source below a predetermined limit.

43. A sensor according to claim 31, wherein said light source produces heat, wherein said sensor has a frame, and wherein said light source is fastened to said frame for conducting heat from said light source to said frame to maintain the temperature of the light source below a predetermined limit.

44. A sensor according to claim 31, wherein said light source has a mounting frame and wherein said light source is located in a cavity of said frame.

45. A sensor according to claim 31, further including at least one light transmitting, optical fiber coupled to at least one of said light source or receiver.

46. A sensor according to claim 31, further including attachment means for attaching the sensor to the body of the subject.

47. Measuring apparatus for determining the amount of one or more light absorbing substances in the blood of a subject, said apparatus comprising:
- a light source emitting light for application to blood containing tissue of the subject, the emitted light of said source having at least two predetermined center wavelengths;
- a receiver receiving light from the tissue and providing output signals responsive to the received light;
- a data storage device storing extinction coefficient data, the stored data including extinction coefficients separately determined for each predetermined center wavelength and light absorbing substance;
- means coupled to said receiver for processing the output signals from the receiver;
- reader means coupled to said data storage device for obtaining extinction coefficient data; and
- calculating means coupled to said processing means and said reader means for determining the amount of light absorbing substance in the blood.

48. Measuring apparatus according to claim 47, further defined as one for determining the relative amount of one or more forms of haemoglobin in the blood of a subject.

49. Measuring apparatus according to claim 48, further defined as one for determining the relative amount of a plurality of forms of haemoglobin in the blood of the subject and wherein said calculating means is further defined as carrying out the determination of the forms of haemoglobin on a time division basis.

50. Measuring apparatus according to claim 47, wherein said data storage device stores sensor identification information for provision to said reader means.

* * * * *

UNITED STATES PATENT AND TRADEMARK OFFICE
CERTIFICATE OF CORRECTION

PATENT NO.   : 6,104,938  
DATED        : August 15, 2000  
INVENTOR(S)  : Huiku et al.

Page 1 of 1

It is certified that error appears in the above-identified patent and that said Letters Patent is hereby corrected as shown below:

<u>Column 21,</u>  
Line 11, after "modulation", insert -- ratio --;  
Line 17, delete "haemoglobin"

Signed and Sealed this

Fourteenth Day of May, 2002

Attest:

Attesting Officer

JAMES E. ROGAN  
*Director of the United States Patent and Trademark Office*